(12) United States Patent
Mclaughlin et al.

(10) Patent No.: US 10,232,106 B2
(45) Date of Patent: Mar. 19, 2019

(54) METHOD AND SYSTEM FOR CHARACTERISING BIOLOGICAL TISSUE

(71) Applicant: The University of Western Australia, Crawley, Western Australia (AU)

(72) Inventors: Robert Ainsley Mclaughlin, Bayswater (AU); Bryden Christopher Quirk, Mount Nasura (AU); Brendan Francis Kennedy, Joondanna (AU)

(73) Assignee: The Unversity of Western Australia, Crawley, Western Australia (AU)

(*) Notice: Subject to any disclaimer, the term of this patent is extended or adjusted under 35 U.S.C. 154(b) by 410 days.

(21) Appl. No.: 14/433,682

(22) PCT Filed: Oct. 4, 2013

(86) PCT No.: PCT/AU2013/001146
§ 371 (c)(1),
(2) Date: Apr. 6, 2015

(87) PCT Pub. No.: WO2014/053026
PCT Pub. Date: Apr. 10, 2014

(65) Prior Publication Data
US 2015/0273135 A1    Oct. 1, 2015

(30) Foreign Application Priority Data
Oct. 4, 2012    (AU) ................... 2012904331

(51) Int. Cl.
*A61B 5/00*    (2006.01)
*A61M 5/00*    (2006.01)
(Continued)

(52) U.S. Cl.
CPC ......... *A61M 5/007* (2013.01); *A61B 1/00165* (2013.01); *A61B 1/00177* (2013.01);
(Continued)

(58) Field of Classification Search
CPC ............ A61B 1/00096; A61B 1/00165; A61B 1/00177; A61B 1/015; A61B 1/043;
(Continued)

(56) References Cited

U.S. PATENT DOCUMENTS

| 3,941,121 A | 3/1976 | Olinger et al. |
| 6,770,070 B1 | 8/2004 | Balbierz |

(Continued)

FOREIGN PATENT DOCUMENTS

| EP | 0187744 | 7/1986 |
| EP | 1213988 | 11/2009 |

(Continued)

OTHER PUBLICATIONS

International Search Report for PCT/AU2013/001146 dated Jan. 31, 2014 (3 pages).

(Continued)

*Primary Examiner* — Mark Remaly
(74) *Attorney, Agent, or Firm* — Michael Best & Friedrich LLP

(57) ABSTRACT

The present disclosure provides a method for characterizing a region of interest within or between biological tissue. The method comprises inserting at least a portion of a probe into the region of interest and directing electromagnetic radiation to the region of interest and receiving electromagnetic radiation from the region of interest using the probe in a direction that is transversal to a length of the probe. Further, the method comprises directing a fluid to the region of interest through a portion of the probe and analyzing received electromagnetic radiation.

18 Claims, 12 Drawing Sheets

(51) Int. Cl.
*A61B 1/00* (2006.01)
*A61B 1/313* (2006.01)
*G01B 9/02* (2006.01)
*A61M 5/32* (2006.01)
*A61B 1/015* (2006.01)
*A61B 1/04* (2006.01)

(52) U.S. Cl.
CPC ............ *A61B 1/015* (2013.01); *A61B 1/3137* (2013.01); *A61B 5/0066* (2013.01); *A61B 5/0068* (2013.01); *A61B 5/0071* (2013.01); *A61B 5/0084* (2013.01); *A61B 5/4839* (2013.01); *A61B 5/4848* (2013.01); *A61B 5/6848* (2013.01); *A61M 5/3291* (2013.01); *G01B 9/0205* (2013.01); *G01B 9/02091* (2013.01); *A61B 1/00096* (2013.01); *A61B 1/043* (2013.01)

(58) Field of Classification Search
CPC ... A61B 1/3137; A61B 5/0066; A61B 5/0068; A61B 5/0071; A61B 5/0084; A61B 5/4839; A61B 5/4848; A61B 5/6848; A61M 5/007; A61M 5/3291; G01B 9/0205; G01B 9/02091
See application file for complete search history.

(56) References Cited

U.S. PATENT DOCUMENTS

| | | |
|---|---|---|
| 2004/0215166 A1 | 10/2004 | Atlas |
| 2008/0033241 A1 | 2/2008 | Peh et al. |
| 2010/0008793 A1 | 1/2010 | McDowell et al. |
| 2010/0076320 A1 | 3/2010 | Petersen et al. |
| 2011/0190662 A1 | 8/2011 | McWeeney |
| 2012/0226166 A1 | 9/2012 | Saadat et al. |

FOREIGN PATENT DOCUMENTS

| | | |
|---|---|---|
| EP | 2148608 | 2/2010 |
| JP | 2009526554 | 8/2007 |
| JP | 2008510586 | 4/2008 |
| JP | 2010142496 | 7/2010 |
| JP | 2010200820 | 9/2010 |
| TW | 201130456 | 9/2011 |
| WO | 01/11409 | 2/2001 |
| WO | 2008/045851 | 4/2008 |
| WO | 2009061483 | 5/2009 |
| WO | 2009155432 | 12/2009 |
| WO | 2010008793 | 1/2010 |
| WO | 2010/104752 | 9/2010 |
| WO | 2012128711 | 9/2012 |
| WO | 2012170401 | 12/2012 |
| WO | 2013/009977 | 1/2013 |

OTHER PUBLICATIONS

International Preliminary Report on Patentability for PCT/AU2013/001146 dated Jan. 15, 2015 (16 pages).
Supplementary European Search Report for Patent Application No. 13844248.8 dated Mar. 29, 2016 (2 pages).
Kennedy et al., "Needle optical coherence elastography for tissue boundary detection", Optics Letters, Jun. 15, 2012, vol. 37 (12), 2310-2312.
Chinese Patent Office Action for Application No. 2013800519002 dated Oct. 8, 2016 (8 pages).
Japanese Patent Office Action for Application No. 2015534882 with English translation dated May 30, 2017 (9 pages).
European Patent Office Action for Application No. 13844248.8 dated May 2, 2018 (5 pages).

METHOD AND SYSTEM FOR CHARACTERISING BIOLOGICAL TISSUE

FIELD OF THE INVENTION

The present invention broadly relates to a method and system for characterising biological tissue and relates particularly to a method and system for characterising biological tissue using an optical imaging technique.

BACKGROUND OF THE INVENTION

Optical imaging techniques such as optical coherence tomography (OCT) or confocal microscopy are frequently used to image biological tissue. Fluids may be introduced into the biological tissue to facilitate the imaging. For example, during OCT imaging of an air-filled lung, the imaging light beam may be distorted or strongly attenuated each time it transitions between an area of tissue and an area filled with air because of the difference in refractive index between the tissue and the air. To reduce such imaging artifacts, the air may be replaced by fluid in the lung lobe being imaged, reducing such artifacts. This is a technique known as bronchoalveolar lavage. In another example, an optical clearing agent such as glycerol may be introduced into a tissue to increase the image penetration depth of an OCT imaging system. In yet another example, a fluorescent contrast agent may be introduced into tissue to enhance the fluorescence of tissue during wide field fluorescence microscopy or confocal microscopy.

Existing methods of fluid introduction for imaging and/or measurement purposes have significant disadvantages. For example, often an excessive amount of the fluid is required, regions other than a region of interest are exposed to the fluid and direction of the fluid to the region of interest and subsequent removal is difficult. There is a need for advancement.

SUMMARY OF THE INVENTION

In accordance with a first aspect the present invention provides a method for characterising a property of a region of interest within or between biological tissue, the method comprising the steps of:
  inserting at least a portion of an elongated probe body of a probe into the region of interest;
  directing a fluid to the region of interest through a fluid opening of the elongated probe body, the fluid opening having a fixed location relative to the elongated probe body;
  directing electromagnetic radiation to the region of interest from the probe and receiving electromagnetic radiation from the region of interest by the probe, the electromagnetic radiation being directed from a location that is fixed relative to the elongated probe body and in a direction that is transversal to the elongated probe body; and
  analysing received electromagnetic radiation to characterise the property of the region of interest.

Embodiments of the present invention have significant advantages. As the step of directing a fluid to the region of interest comprises directing the fluid through a fluid opening of the elongated probe body, it may be possible to direct the fluid substantially exclusively into the proximity of the region of interest. Further, as the electromagnetic radiation is directed in a direction that is transversal to the elongated probe body, it is possible to obtain data that corresponds to multiple dimensions (for example by translational and/or rotational movement of the probe during data detection).

The step of inserting at least a portion of the elongated probe body into the region of interest typically comprises contacting the biological tissue with the elongated probe body.

The step of directing the electromagnetic radiation typically is conducted when at least a portion of the fluid is present in the region of interest.

The step of directing the electromagnetic radiation may be conducted multiple times after an onset of directing the fluid to the region of interest and/or after completion of the step of directing the fluid. Alternatively, the step of directing the electromagnetic radiation may be conducted continuously during a predetermined period of time, such as less than 0.01, 0.1, 0.5, 1, 2, 5, or 10 minutes after the onset of directing the fluid and/or after completion of directing the fluid.

The method may also comprise moving the elongated probe body in the biological tissue during, after of before directing the electromagnetic radiation. For example, the elongated probe body may be rotated about an axis of the elongated probe body and/or translated along the axis.

The step of directing the fluid may also be conducted during first and second time intervals and may be repeated periodically.

In one embodiment the step of directing the fluid comprises directing the fluid in a direction that is transversal to the elongated probe body.

The step of directing the electromagnetic radiation may comprise directing and receiving the electromagnetic radiation through the fluid opening of the probe.

Alternatively, the step of directing the electromagnetic radiation may comprise directing and receiving the electromagnetic radiation through a portion that is substantially transmissive for the electromagnetic radiation or a though a further opening of the elongated probe body. In either case the fluid opening and a position from which the electromagnetic radiation is directed may be in close proximity to each other, such as within a distance of less than 30, 20, 10, 5, 2, 1, 0.5, 0.1 or even 0.01 mm.

The region of interest may be a region in an in-vivo or ex-vivo environment. In one specific example the region of interest is an intravascular region. In another specific example the region of interest is an endoscopic region or a region within tissue without an epithelial or endothelial layer between the probe and the region of interest.

The method may comprise imaging or otherwise obtaining information concerning the region of interest using any suitable technique, such as optical coherence tomography (OCT) imaging and/or confocal imaging and/or fluorescence microscopy and/or multi-photon microscopy and/or diffuse optical tomography and/or total internal reflection fluorescence microscopy and/or phase contrast microscopy and/or stimulated emission depletion microscopy and/or near-field scanning optical microscopy and/or differential interference contrast microscopy and/or second harmonic imaging microscopy and/or reflectance spectroscopy.

In one embodiment the method comprises characterising the property of the region of interest by imaging at least a portion of the biological tissue within the region of interest. The fluid may have a refractive index that is selected such that refractive index differences within the region of interest are changed when the fluid is present.

The step of directing the fluid may also comprise flushing the region of interest of undesirable material to increase a depth of view.

Additionally or alternatively, the step of directing the fluid may comprise directing a fluid that influences an optical property of a further fluid (such as blood) of the region of interest in a manner such that a depth of view is increased.

Further, the step of directing the fluid may comprise directing an optical clearing agent or an optical contrast agent to the region of interest.

The step of directing the fluid may also comprise directing a fluid that comprises a dye and/or label into the region of interest, the dye being selected to accumulate at selected portions within the region of interest.

In one example the step of directing the fluid comprises directing a fluid comprising of nano-particles that alter the optical properties of tissue. Such nanoparticles may be functionalized so as to preferentially bind to a subset of tissue types.

The fluid, which may generally be a gas or a liquid, may also comprise a therapeutic agent.

The step of directing the electromagnetic radiation may comprise imaging at least a portion of the region of interest to identify a specific region of interest. Further, the step of directing the fluid to the region of interest may comprise directing the therapeutic agent to the identified specific region of interest and the step of directing the electromagnetic radiation may also comprise monitoring an effect of the therapeutic agent on the identified specific region of interest.

The step of directing the electromagnetic radiation may also comprise receiving electromagnetic radiation from the region of interest at a multitude of times and the step of analyzing the received electromagnetic radiation may comprise determining a difference between the electromagnetic radiation received at respective times or time intervals.

The method may also comprise directing the fluid into the region of interest and thereafter imaging the region of interest for a predetermined period of time (either in intervals or continuously) to detect changes caused by changed conditions to which the biological tissue is exposed.

In one embodiment the method comprises characterising a physical property, such as a mechanical property of the biological tissue within the region of interest. For example, the mechanical property may be an elasticity, a viscosity, a viscoelasticity, a compressive strength, a tensile strength or a Young's modulus. Characterising a mechanical property of the biological tissue may comprise characterising a displacement of the biological tissue within the region, wherein the displacement results from insertion of the fluid. The step of directing the fluid may comprise directing a fluid at a plurality of times. For example, fluid delivery may be periodically repeated and may be pulsed. The method may comprise characterizing the mechanical property of the biological tissue within the region of interest at a multitude of times, such as in periodic intervals.

In another embodiment the step of directing the fluid comprises directing a fluid that comprises fluorescently-labelled molecules, such as antibodies, into the region of interest and the step of directing the electromagnetic radiation comprises detecting fluorescence radiation from the region of interest for example to obtain a fluorescence image of the region of interest. In this embodiment the method may comprise imaging before directing the fluid (to detect intrinsic or auto-fluorescence) and/or during and/or after directing the fluid to the region of interest. This embodiment of the present invention may provide information about preferred attachment regions of the antibodies at the region of interest, which can be used to characterise the property of the region of interest. Further, the method may comprise detecting fluorescence radiation during a change in a property of the fluorescence radiation (such as a change in intensity) to determine the change in the property.

In a further embodiment the step of directing the fluid comprises directing a fluid that comprises nanoparticles into the region of interest and the step of directing electromagnetic radiation to the region of interest. In this embodiment the nano-particles have a reflectivity that is either higher or lower than that of the region of interest. The method may comprise OCT imaging of the region of interest before directing the fluid to the region of interest and/or during and/or after the step of directing the fluid to the region of interest. This embodiment may provide information about preferred attachment regions of the nanoparticles at the region of interest, which can be used to characterise the region of interest.

In yet another embodiment the method comprises OCT or fluorescence imaging of the region of interest during and/or after directing the fluid to the region of interest in order to monitor clearing of the fluid. In this embodiment the method may comprise determining a rate at which the fluid is cleared in the region of interest, which may provide information about how the fluid may be cleared, for example through the lymphatic system and/or through the blood vessels. For example, in an area of invasive cancer, much of the structure of the region of interest may destroyed, and the fluid will clear at a rate that is different to the rate at which the fluid will clear in a healthy region of interest.

In accordance with a second aspect the present invention provides a method for characterising a region of interest within or between biological tissue, the method comprising the steps of:
  inserting at least a portion of a probe into the region of interest;
  directing electromagnetic radiation to the region of interest using the probe;
  receiving first and second types of electromagnetic radiation from the region of interest using the probe;
  directing a fluid to the region of interest through a fluid opening of the probe; and
  analysing the received first and second types of electromagnetic radiation.

In one embodiment the first type of the received electromagnetic radiation is radiation that has been directed to the region of interest by the probe and is reflected by the region of interest. The second type of electromagnetic radiation may be another suitable type of electromagnetic radiation, such as fluorescence radiation that is generated by the region of interest or by fluorescence markers that are present in the region of interest. For example, the method may comprise (simultaneous or successive) OCT imaging and fluorescence imaging.

In accordance with a third aspect the present invention provides a system for characterising biological tissue, the system comprising:
  a probe comprising:
    an elongated probe body for at least partial insertion into a region of interest within or between the biological tissue, the elongated probe body having at least one fluid opening that is fixed relative to the elongated probe body and that is in use positioned within or between the biological tissue;
    an optical element comprising an optical waveguide positioned at least partially within the elongated probe body, the optical element being arranged to enable transmission of electromagnetic radiation between the probe and the region of interest and from a position that is fixed relative to the elongated probe body;

a conduit for delivery of a fluid through the at least one fluid opening of the probe body to the region of interest, the conduit being at least partially positioned within the probe body; and a fluid reservoir coupled to the conduit;

wherein the system is arranged to transmit the electromagnetic radiation between the probe and the region of interest in a direction that is transversal to the elongated probe body.

The probe of the system may be arranged such that the fluid can be delivered into the region of interest during, immediately before and/or after imaging or otherwise providing information using the optical element such that the fluid is present during the imaging or otherwise providing the information.

The at least one fluid opening may be at a side portion of the elongated probe body such that the system is arranged to direct the fluid in a direction that is transversal to the elongated probe body.

The probe may be arranged such that the transmission of the electromagnetic radiation between the probe and the region of interest is conducted through the at least one fluid opening.

Alternatively, the elongated probe body may comprise at least one portion that is substantially transmissive for the electromagnetic radiation or the probe body may comprise at least one further opening through which the electromagnetic radiation is in use directed. In either case a location from which in use the electromagnetic radiation is directed typically is fixed relative to the probe body and is in the proximity of the at least one fluid opening. For example, the location form which the electromagnetic radiation is directed may be within a distance of less than 30, 20, 10, 5, 2, 1, 0.5 0.1, or even 0.01 mm of the at least one fluid opening.

The at least one fluid opening and/or the at least one further opening may have a diameter of less than 5, 2, 0.5 or even 0.1 mm.

The probe body may be formed from a rigid material, such as stainless steel. Alternatively, the probe body may also be formed from, or comprise, a flexible material, such as a suitable polymeric material.

The system may be arranged such that the fluid, which may comprise a plurality of component fluids and may be a liquid or a gas, can be directed from the elongated probe body into the region of interest during, or immediately before imaging or otherwise obtaining information using the optical element. Alternatively or additionally, the system may be arranged such that the fluid or a further fluid, such as a therapeutic agent, can be directed from the probe to the region of interest after imaging or otherwise obtaining information for example for treatment purposes.

In one specific embodiment the probe is a needle probe. Alternatively, the probe may for example be an intravascular probe or an endoscopic probe.

The conduit may be coupled directly or indirectly to the fluid reservoir. For example, the fluid reservoir may be positioned at a remote location and the conduit may be coupled indirectly to the fluid reservoir via a further conduit.

In one embodiment the system is arranged for optical coherence tomography (OCT) imaging. Alternatively, the system may be arranged for any other suitable technique for imaging or otherwise providing information using the optical element. Examples of some suitable imaging techniques include confocal imaging, fluorescence imaging, multi-photon microscopy, diffuse optical tomography, total internal reflection fluorescence microscopy, phase contrast microscopy, stimulated emission depletion microscopy, near-field scanning optical microscopy, differential interference contrast microscopy, second harmonic imaging microscopy and/or reflectance spectroscopy.

In one embodiment the system is arranged for imaging or otherwise providing information using two or more of such techniques. For example, the probe may be arranged for (simultaneous or successive) OCT imaging and fluorescence imaging. In this case the optical element may be one of two optical elements, but the probe may also comprise a single optical element that is arranged for two or more imaging techniques.

The probe may be arranged for characterising the region of interest in an in-vivo or ex-vivo environment.

The waveguide may be an optical fibre and typically is a single-mode optical fibre.

A person skilled in the art will appreciate that the present invention is not limited to use in medical applications involving humans or human tissue, but can alternatively also be used for characterising animal tissue or plant matter or synthetic structures.

The invention will be more fully understood from the following description of specific embodiments of the invention. The description is provided with reference to the accompanying drawings.

DETAILED DESCRIPTION OF SPECIFIC EMBODIMENTS

Embodiments of the present invention relate to a system and a method for characterising biological tissue using optical imaging techniques with the localised application of fluid.

The fluid may be used to increase a depth of view or otherwise increase visibility. For example, the fluid may be a clearing agent or may be arranged to flush a region between tissue portions. Alternatively, the fluid may comprise a contrast agent.

The application of the fluid can also be used to decrease the difference in optical properties between tissues. For example, optical coherence tomography (OCT) imaging of the lung parenchyma has a relatively small penetration depth because of the large difference in refractive index between the air-filled compartments within the parenchyma and parenchymal tissue. Filling the alveoli and bronchioles with a fluid, for example saline, replaces the air and reduces the difference in refractive index thus allowing the light to penetrate more deeply and increase the imaging depth of OCT.

The effect of the fluid on the optical properties can also be indicative of the effectiveness with which the fluid can penetrate into the tissue. For example, dyes may be used to assess cellular membrane permeability in muscle tissue, as the dye may accumulate in areas where the cellular membrane has deteriorated. Such deterioration can be indicative of necrosis, and this technique may be used to differentiate between healthy and necrotic tissue.

The system in accordance with embodiments of the present invention comprises a probe that is arranged to allow both the local application of the fluid to the region of interest and characterisation of the region of interest, and which may include imaging or otherwise obtaining information concerning a property of the biological tissue. For example, the property may be a mechanical property such as an elasticity, a viscosity, a viscoelasticity, a compressive strength, a tensile strength or a Young's modulus.

Figure 1:
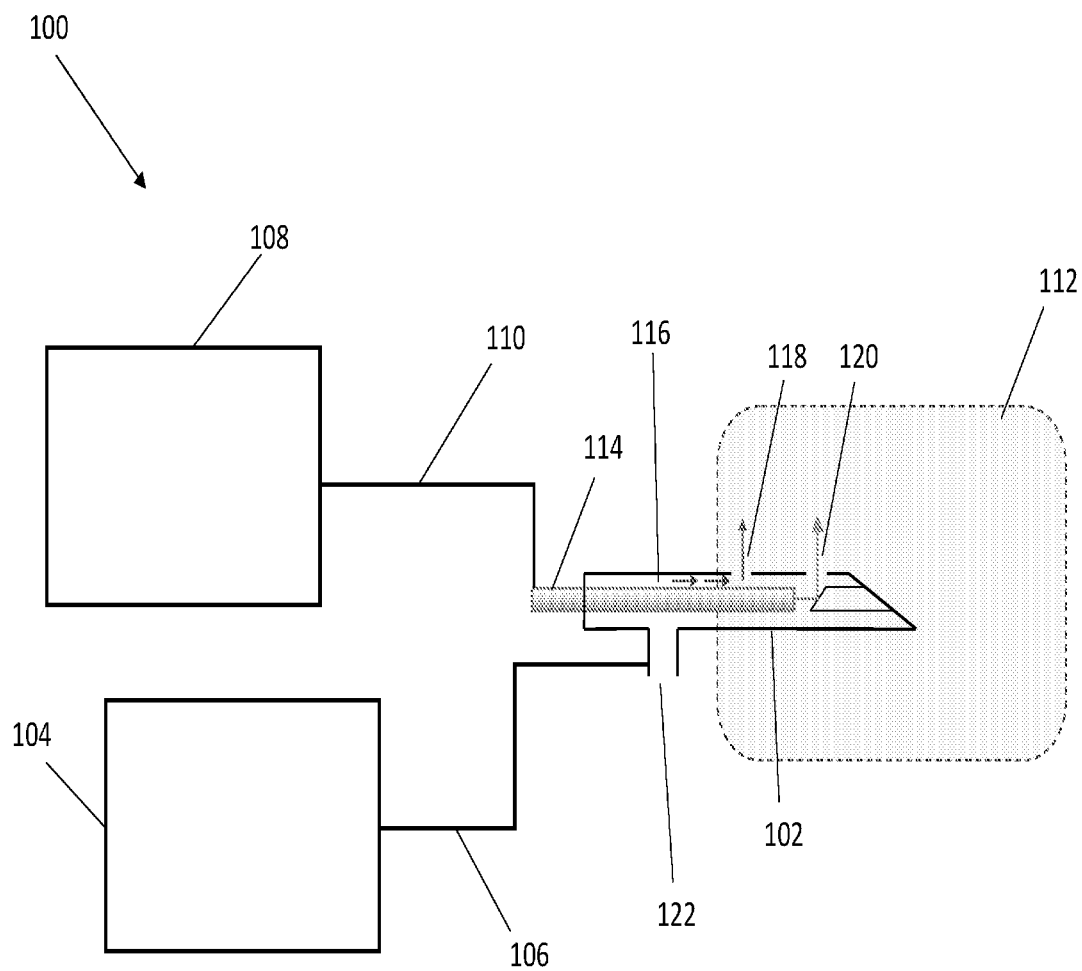
FIG. 1 is a schematic representation of a system for characterising a region within or between biological tissue in accordance with an embodiment of the present invention.

FIG. 1 shows a system 100 comprising of a needle probe 102 for insertion within or between biological tissue 112. In this particular embodiment of the invention, the needle probe 102 is a hypodermic needle probe that may be used for in-vivo and ex-vivo applications.

The needle probe 102 comprises an optical element 114 that is coupled to an analyser 108 via coupling 110. In this particular embodiment of the invention, the analyser 108 is arranged for processing OCT data and the optical element 114 is an optical fibre, which transmits electromagnetic radiation through an optical window 120 within a wall of the body of the needle probe 102 to a region of interest. The electromagnetic radiation is light having a wavelength in the near infrared range, but a person skilled in the art will appreciate that alternatively light having a wavelength in another wavelength range may be used.

The optical window 120 may be formed from any material that is transmissive for the electromagnetic radiation and may also be replaced by an opening. The needle probe 102 has an exterior portion that is formed from a biocompatible material.

The needle probe 102 also comprises of a fluid conduit 116, which is formed adjacent to a portion of the optical fibre 114 and is coupled to a fluid reservoir 104 through suitable piping or a suitable hose 106. The fluid reservoir 104 provides the fluid for delivery through fluid inlet 122 to the conduit 116 and through fluid outlet 118 into the region of interest. The fluid outlet 116 is, in this embodiment, a simple opening, but may also comprise a filter.

Figure 2:
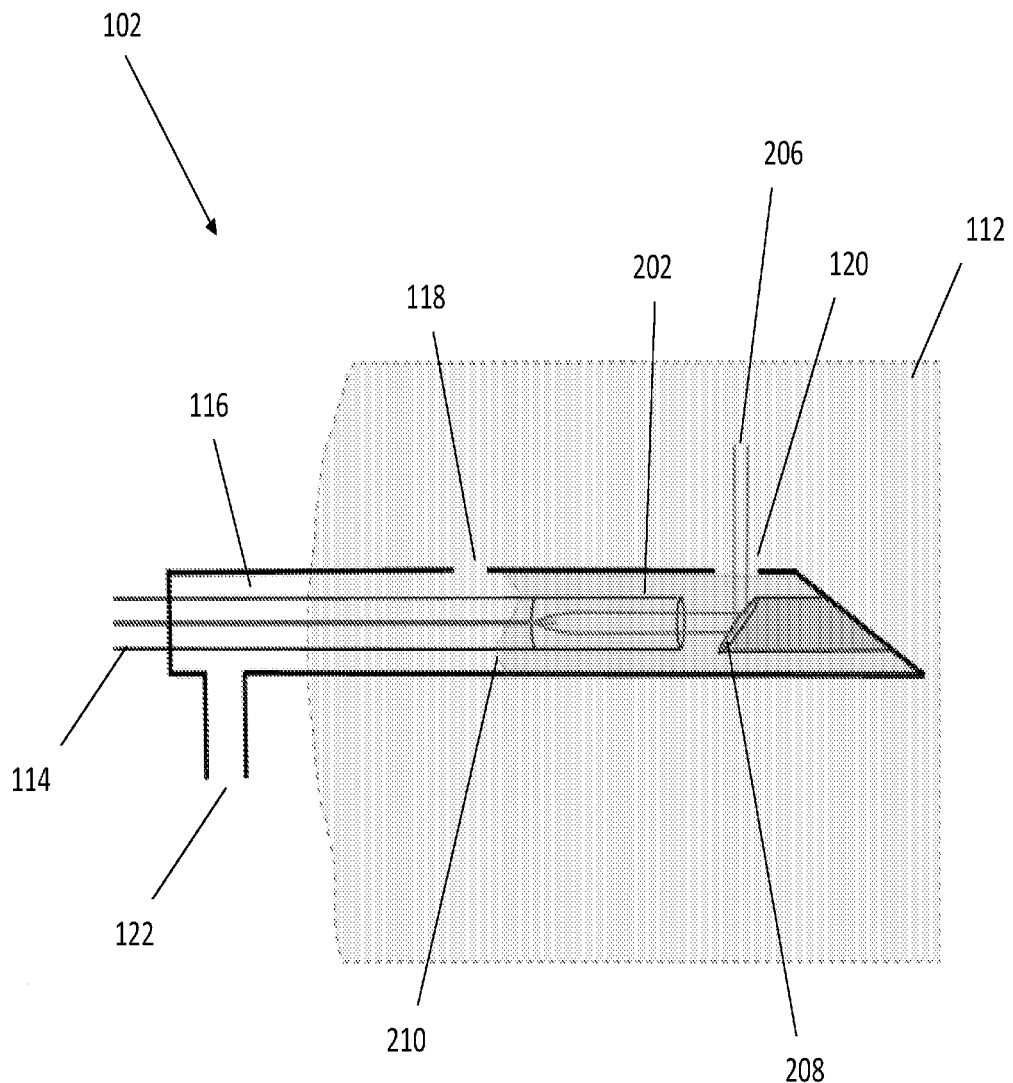
FIGS. 2 to 4 are schematic representations of probes that the system shown in FIG. 1 may comprise.

The needle probe 102 will now be described in more detail with reference FIG. 2. In this particular embodiment, the optical fibre 114 is coupled to a focusing element 202 to direct the light 206 to a reflector 208, which redirects the light 206 through the optical window 120 on the side of the needle probe 102 to the region of interest in biological tissue 112. The optical window 120 and optical components may alternatively be arranged for forward viewing instead of side viewing.

The focusing element 202 and the reflector 120 are in this example rigidly attached to a tubular body of the needle probe 102 using a suitable optical adhesive 210.

The fluid opening 118 is in line with and in close proximity to the optical window 120. The fluid can be applied to the region of interest during or immediately before imaging (or otherwise obtaining information) in a manner such that at least a portion of the fluid is present in the region of interest during the imaging (or otherwise obtaining the information). Alternatively or additionally the fluid may be applied to the region of interest immediately after imaging (or otherwise obtaining information). The fluid opening may also be positioned at another suitable location and may also be one of a plurality of fluid openings. Each of the plurality of fluid openings may be conduits for one or more fluids.

In this embodiment a tubular body of the needle probe 102 is formed from stainless steel.

A person skilled in the art will appreciate that the probe may take many different forms. For example, the probe may have dimensions similar to those of the needle probe 102, but may be an intravascular probe arranged for insertion into blood vessels.

Figure 3:
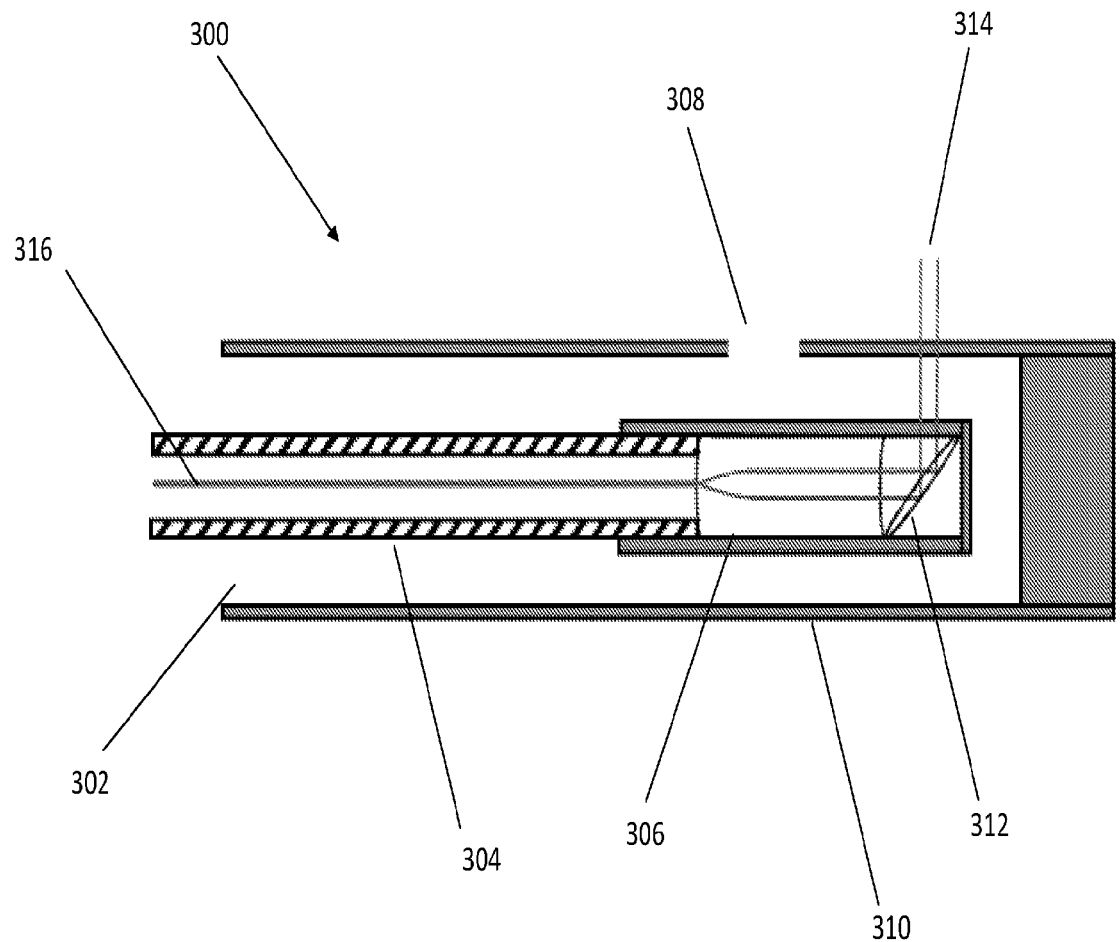

Referring now to FIG. 3, there is shown a probe 300 in accordance with another embodiment of the present invention. The probe 300 may replace the needle probe 102 shown in FIG. 1. In this example the probe 300 is an endoscopic probe that is arranged for OCT imaging. The probe 300 comprises an optical fibre 316 that is enclosed in a stainless steel coil 304 and focusing optics 306 positioned in a transparent catheter 310. A generated light beam 314 is reflected by a prism or mirror 312 and is transmitted through the transparent catheter 310 of the endoscopic probe 300. A fluid is directed through conduit 302 and fluid outlet 308 into a region of interest (not shown).

Figure 4:
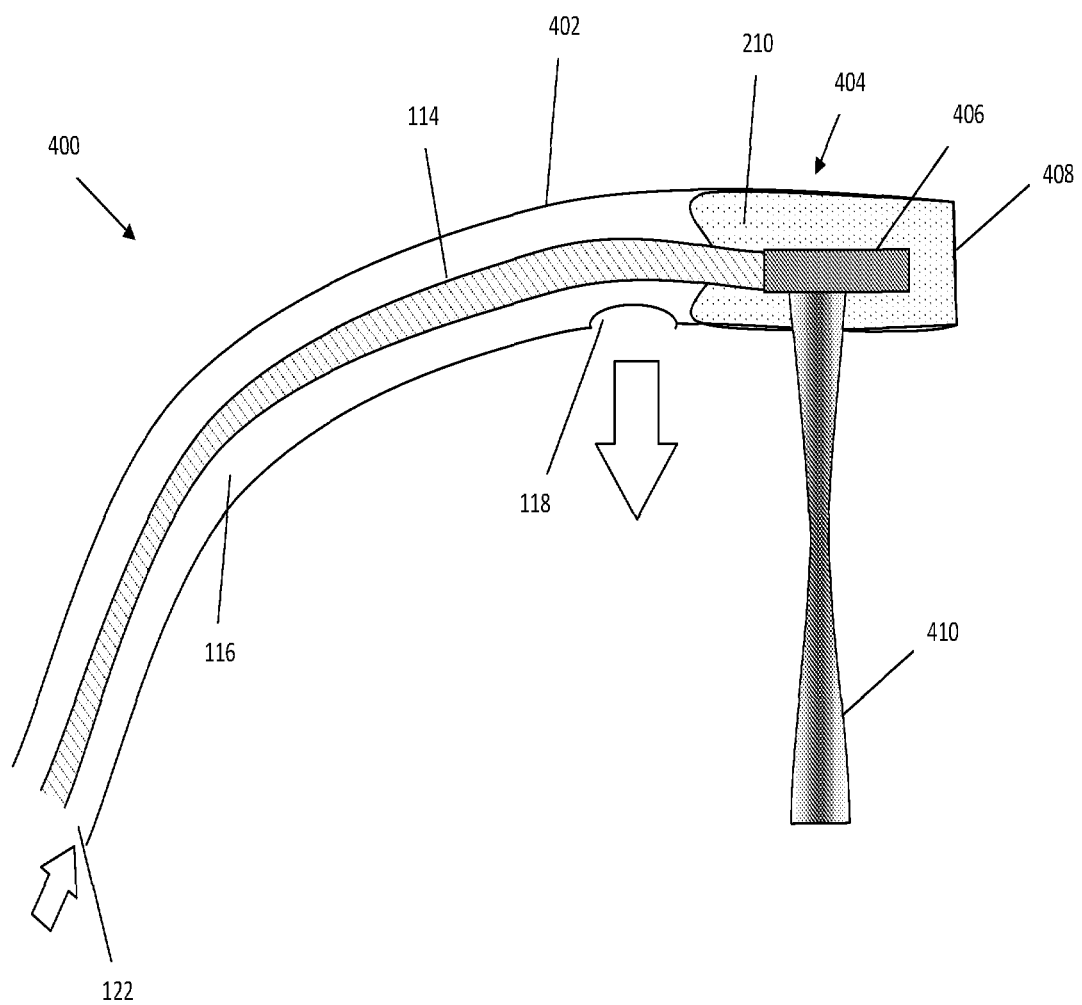
Figure 5:
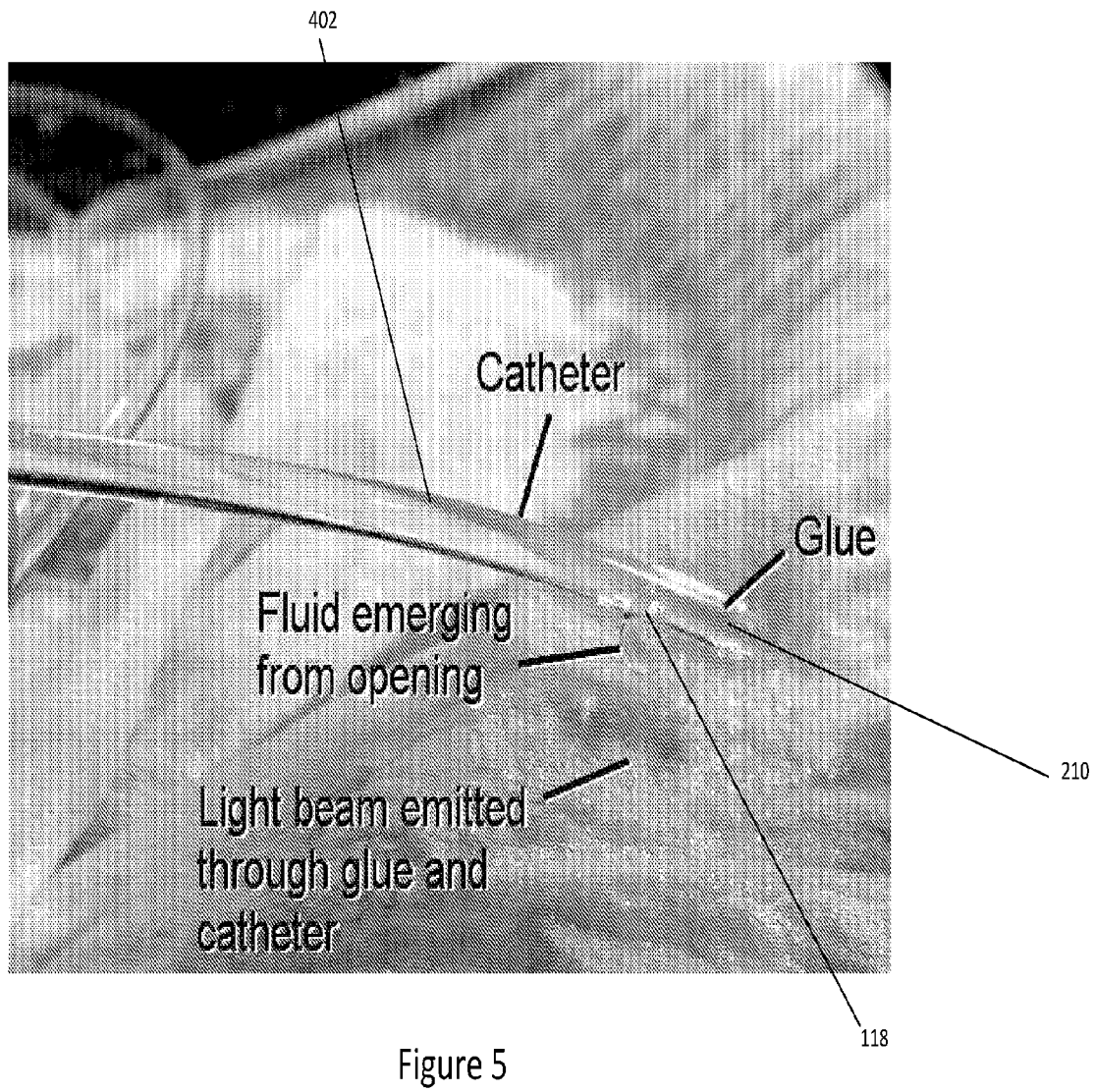
FIG. 5 is a photographic image of a probe in accordance with an embodiment of the present invention.

Referring now to FIGS. 4 and 5, a probe in accordance with a further embodiment of the present invention is described. The probe 400 may also replace needle probe 102 shown in FIG. 1. In this example the probe 400 is an endoscopic or intravascular probe arranged for OCT imaging. The probe 114 comprises an optical fibre 114 encased in a catheter 402 having a fluid conduit 116, fluid inlet 122 and fluid outlet 118 in much the same manner as other embodiments of the invention previously described. However the catheter 402 is a flexible transparent catheter which encases the optical fibre 402.

At the distal end 404 of the probe 400 an optical adhesive 210 is used which occupies a region inside the flexible catheter 402 from the end 410 of the catheter to an area falling short of the fluid outlet 118 of the catheter 404 so that the outlet 118 is not impeded by the optical adhesive 210. The optical adhesive 210 rigidly encases focusing optics 406 which redirects light 410 transmitted from the optical fibre 114 outward towards the region of interest of biological material. The optical adhesive 210 is liquid impermeable and may be any suitable adhesive, such as glue, capable of transmitting light 410 from the optical fibre 114. Depending on the desired purpose and result the type of glue and material for the flexible catheter 402 chosen may be such that their refractive indexes are closely matching so as to minimise distortion of the optical beam or light 410 as it transmits out of the probe 400.

Thus, the probe 400 can be inserted into a region of biological tissue and fluid can be expelled from the fluid conduit 122 into the region of biological tissue before or during OCT scanning of the biological tissue. FIG. 5 is a photographic image of the probe in accordance with the embodiment shown in FIG. 4. The flexible nature of the catheter 402 and thus the probe 400 makes it suitable for endoscopic or intravascular circumstances since the size of an organ or blood vessel may require a certain amount of flexibility and manoeuvrability from the probe 400.

Figure 6:
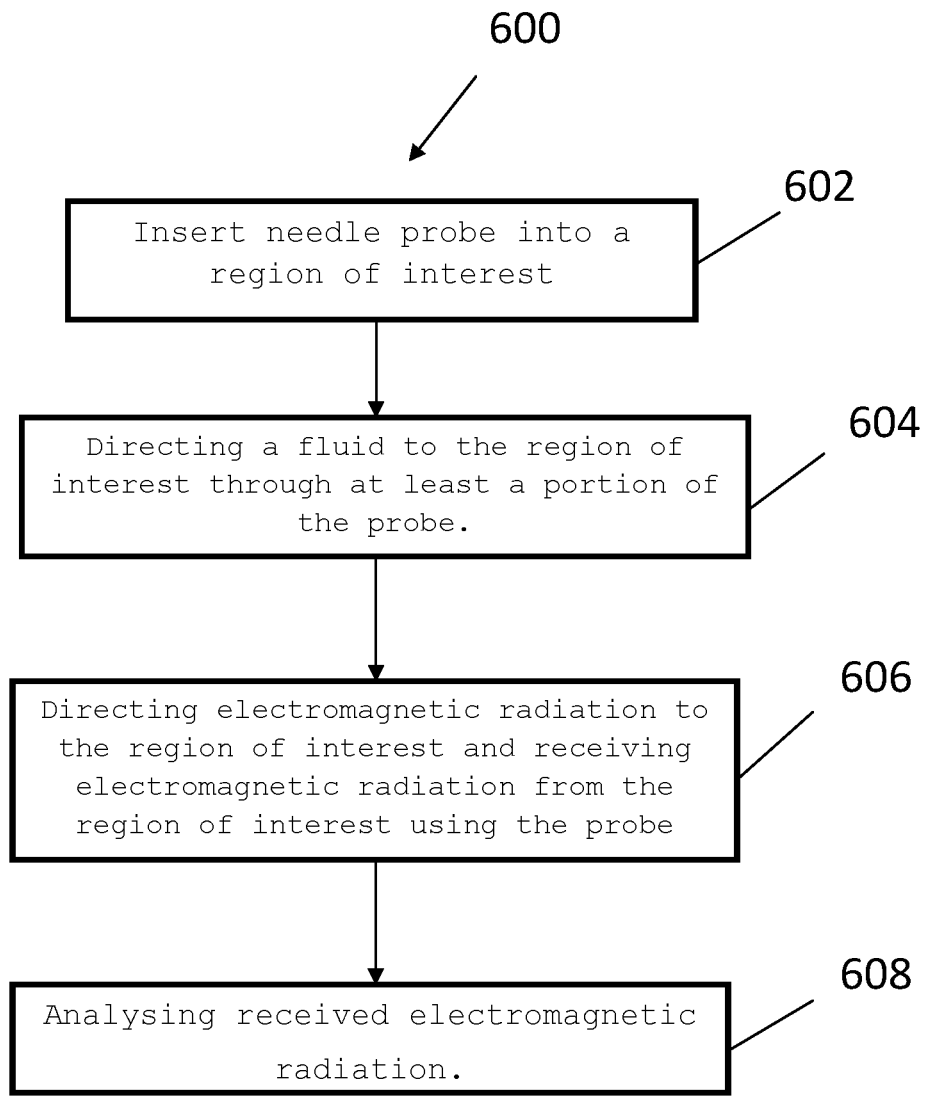
FIG. 6 is a flow chart of a method in accordance with an embodiment of the present invention.

FIG. 6 shows a flow diagram of a method 600 for characterising a region of interest within or between biological tissue in accordance with an embodiment of the present invention. The method 600 comprises the initial step 602 of inserting a probe, such as the needle probe 102 or the endoscopic probes 300 or 400, into the region of interest. The probe is inserted into a depth that is sufficient such that the optical window and the fluid outlet are within or adjacent to the region of interest. This allows for both the fluid and the electromagnetic radiation to be directed locally into the region of interest. The needle probe may be completely surrounded by biological tissue or may be partially positioned within a space defined by wall portions formed by the biological tissue.

Step 604 directs a fluid to the region of interest through a fluid outlet of the probe in a manner such that at least a portion of one or more of a plurality of fluids is present during imaging or otherwise obtaining information concerning the region of interest. For example, the fluid may be directed into the region of interest immediately before and/or during imaging. Step 606 directs electromagnetic radiation to the region of interest and receives electromagnetic radiation from the region of interest through the optical window of the probe. In this embodiment this step comprises OCT imaging, but may alternatively or additionally also comprise other forms of imaging, such as confocal imaging.

Step 408 analyses the received electromagnetic radiation to characterise the region of interest. In addition, the method 400 may comprise directing one or more other fluids into the region of interest after imaging or otherwise obtaining information concerning the biological tissue, and which may include injecting a therapeutic agent to treat identified diseased tissue.

Referring back to FIGS. 1 to 6, specific embodiments and applications of the method 600 are now described. In one example the fluid is saline solution and injected into a body lumen, such as a portion of the lung, to replace air in the lung in a manner such that refractive index differences are reduced within the region of interest resulting in an increase in imaging depth for OCT imaging. A person skilled in the art will appreciate that a variety of fluids other than a saline solution may also be used.

In another embodiment the fluid is used to flush the region of interest or to change a property of a body fluid such that the imaging depth is increased.

In a further embodiment, the method 600 is used to characterise mechanical properties of the tissue within the region of interest. The injection of the fluid, which may be a gas or a liquid, temporarily increases a pressure within the region of interest which consequently elicits a strain in the tissue portions in the region of interest. The pressure and the change in strain with time may be used for elastography studies by acquiring a series of images at times at which the tissue was exposed to a plurality of one or more pressures. By tracking the movement of the tissue, it is possible to calculate the displacement that the tissue undergoes. When a sample region contains more than one type of tissue, for example diseased tissue and healthy tissue, elastography may be used to identify the extent of diseased tissue by deriving an estimate of the local strain. The fluid expelled from the probe can be used to apply a force to the region of interest such that the system may provide information for generating an elastogram.

Further, the fluid may be applied to change the mechanical properties of the biological tissue. For example, the viscoelastic properties of articular cartilage are predominantly governed by the flow of extracellular fluid. Increasing the amount of fluid within the cartilage will change the viscoelastic properties of the tissue. Consequently, the method 600 may be used to differentiate between tissue types by analysing a change in mechanical properties.

The electromagnetic radiation detected by the probe will emanate from a subset of the region of interest. For example, if the probe is a side-facing OCT needle probe, then back-scattered near-infrared light will be detected from locations which lie near a one-dimensional line which passes through the imaging window and is orientated along the direction of the light beam. By moving the probe, a collection of such measurements may be aggregated to form a multidimensional data set. For example, rotating the probe will enable the collection of data within a two dimensional plane, and hence the generation of a two dimensional data set. Both rotating and translating the probe, a three dimensional data set may be acquired.

Referring now to FIGS. 7 to 12, embodiments of the present invention are described in further detail with reference to specific examples.

Figure 7:
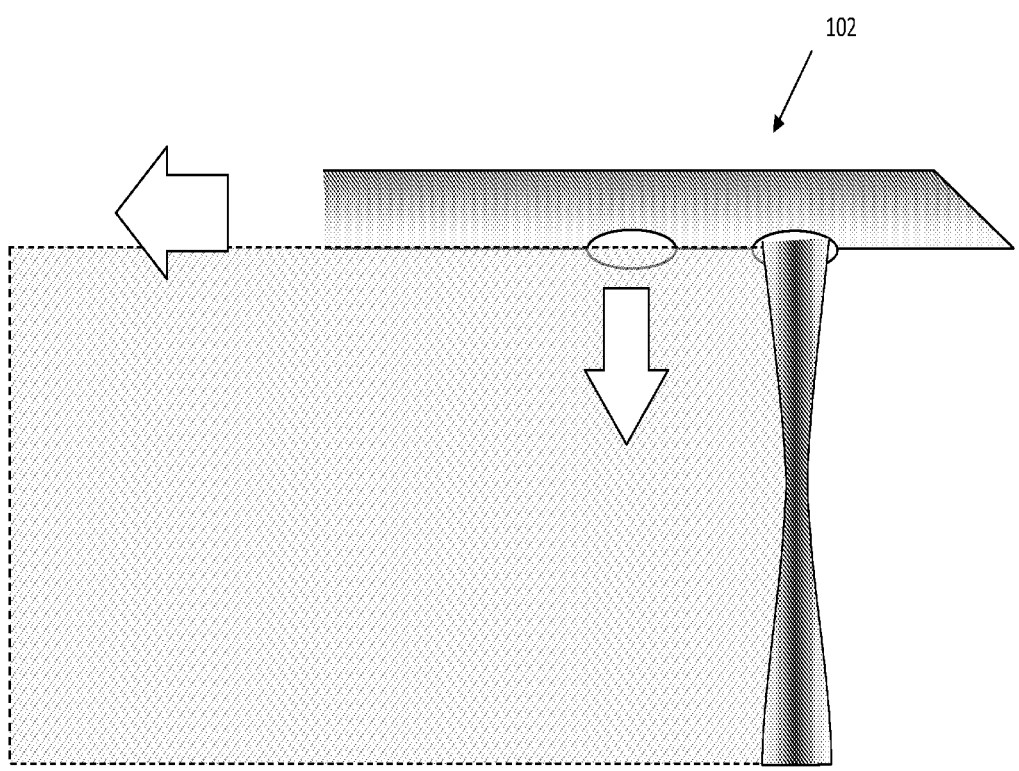
FIGS. 7 to 12 illustrate examples that relate to embodiments of the present invention.

Example 1: Optical Coherence Tomography Imaging—Moving Probe and Injection of Different Fluids FIG. 7 shows a needle probe 102 in accordance with embodiments of the invention shown in FIGS. 1 and 2. In this example the needle probe 102 is inserted into an ex vivo porcine (pig) lung sample and OCT images were captured, as shown in FIGS. 8-11. The images were taken for respective conditions applied during OCT scanning.

The needle probe 102 used in this example was, more specifically, a 22-gauge OCT probe with an outer diameter 720 μm. As previously mentioned the needle probe 102 comprises optical element 114, optical fibre (not shown) inside the probe 102, optical focusing element (not shown) and optical window 120 within the wall of the body of the needle probe 102 to a region of interest of biological tissue 112. The needle probe 102 further comprised a channel through which fluid could be delivered through a second opening or fluid outlet 118 in the needle wall.

In this example the needle probe 102 was interfaced to a swept-source OCT scanner for imaging, and to a fluid reservoir for the introduction of fluid to the region of interest 112. The connection to the fluid reservoir was configured so that the reservoir could be changed during operation. This allowed the injection of different fluids without removing the needle probe 102 from the biological tissue sample.

The images shown in FIGS. 8-11 were acquired as the needle probe 102 was retracted from the region of interest 112, thus generating 2D images adjacent to the path of the needle retraction 702.

The following sequence of scans was acquired:
Pre-injection scan: an OCT scan was acquired of the biological tissue 112 prior to the injection of any fluid.
Saline: saline fluid was injected through the needle probe 102 during image acquisition, providing for improved image penetration.
Air: gaseous air (not fluid) was injected through the needle probe 102, demonstrating the ability to deliver a gas during scanning.
Glycerol: liquid glycerol was injected through needle probe 102 during scanning, demonstrating use of a different fluid to saline and providing improved image penetration depth over saline.

The results of this experiment will now be discussed in more detail.

Figure 8:
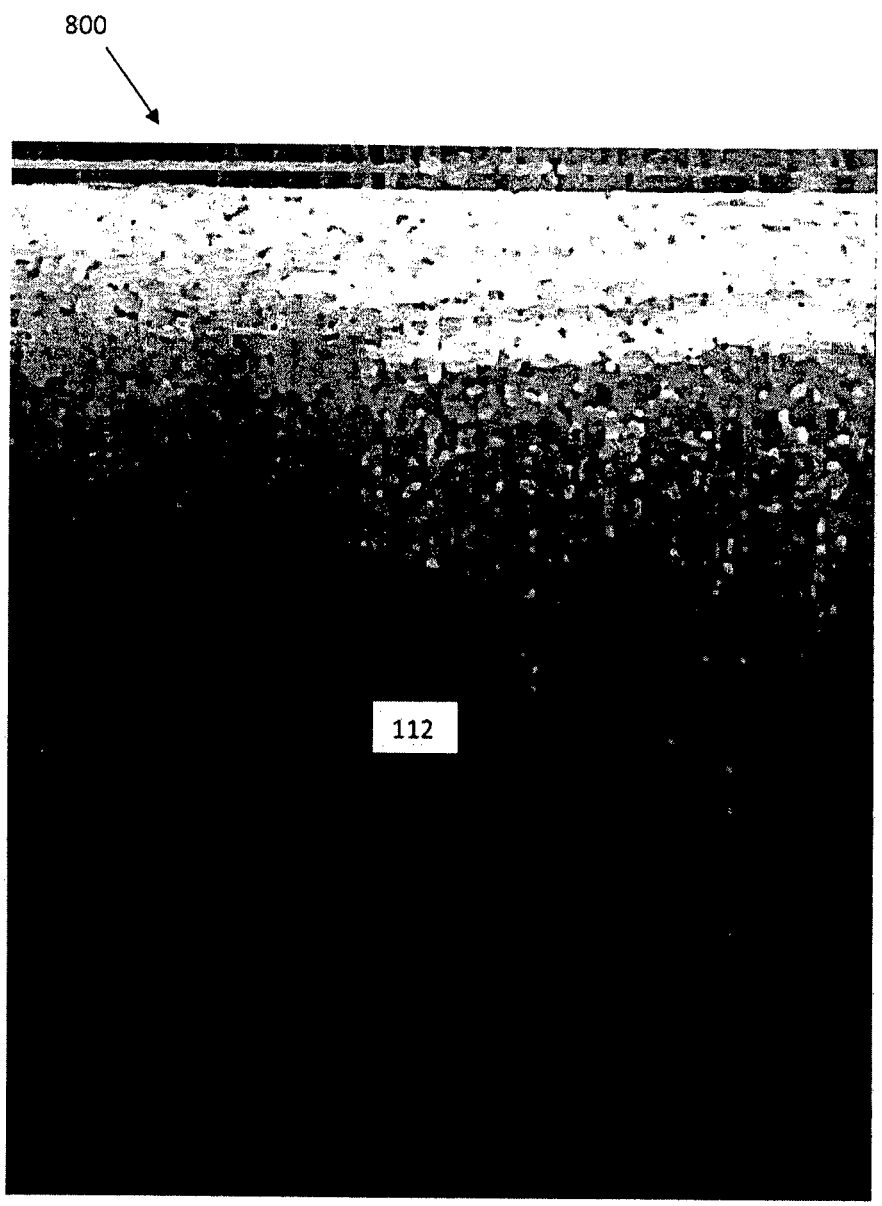

FIG. 8 shows an image 800 of the lung sample 112 acquired with the OCT needle probe 102 prior to the introduction of any fluid through the needle probe 102. Note that alveoli and airways in the imaging plane have collapsed and no discernible lung structures are visible.

Figure 9:
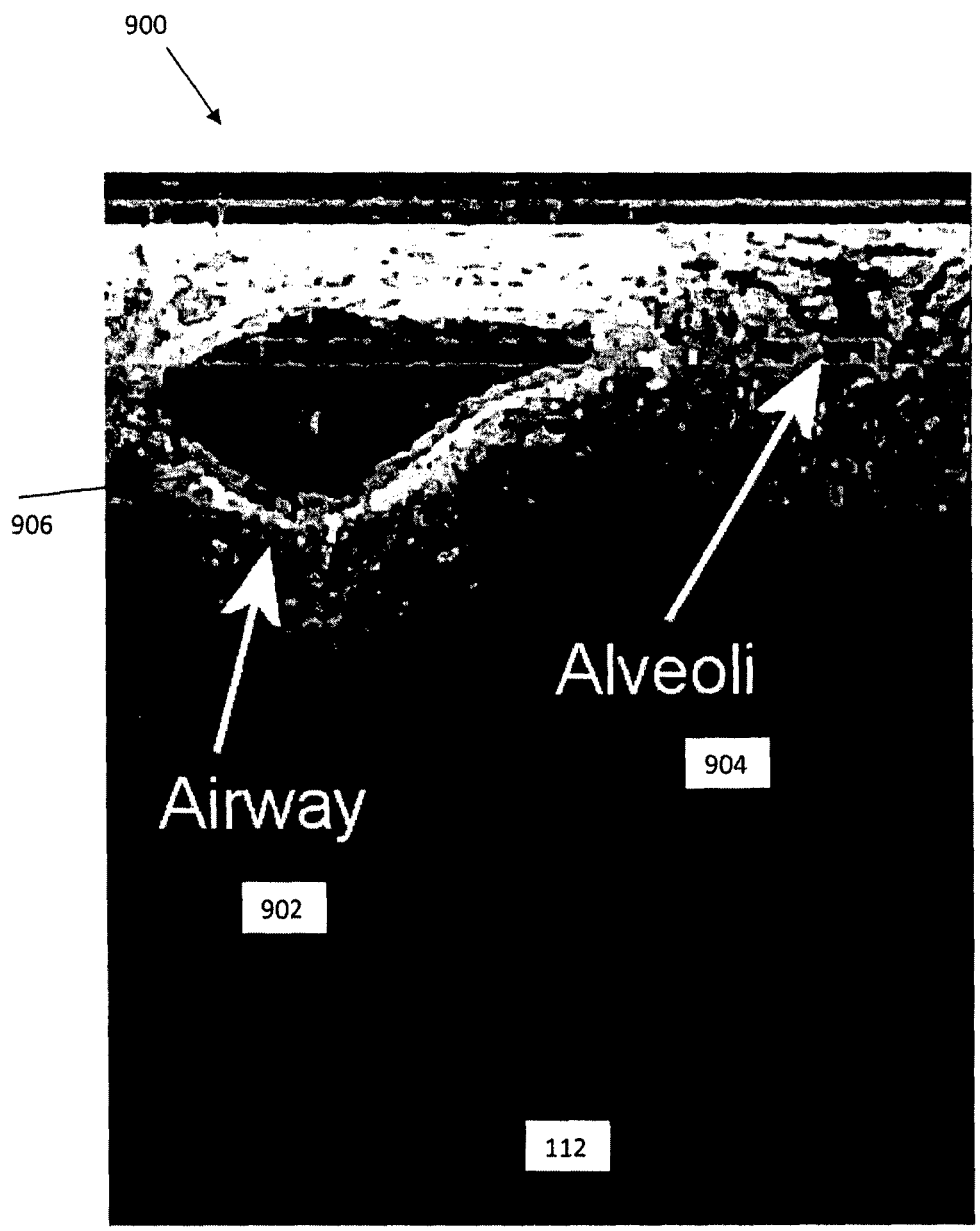

FIG. 9 shows an image 900 acquired by the needle probe 102 of an adjacent area of the lung sample 112 during injection of saline, showing a cross-sectional view of an airway 902 on the left of the image, and a region of alveoli 904. Note that the layered structure 906 of the tissue 112 in the airway wall is also visible. Infusion of saline into the tissue 112 has replaced the air in the adjacent lung tissue. This has both improved the image penetration depth, and allowed collapsed airway and alveoli structures previously seen in FIG. 8 to re-open, thus allowing imaging of their structure.

Figure 10:
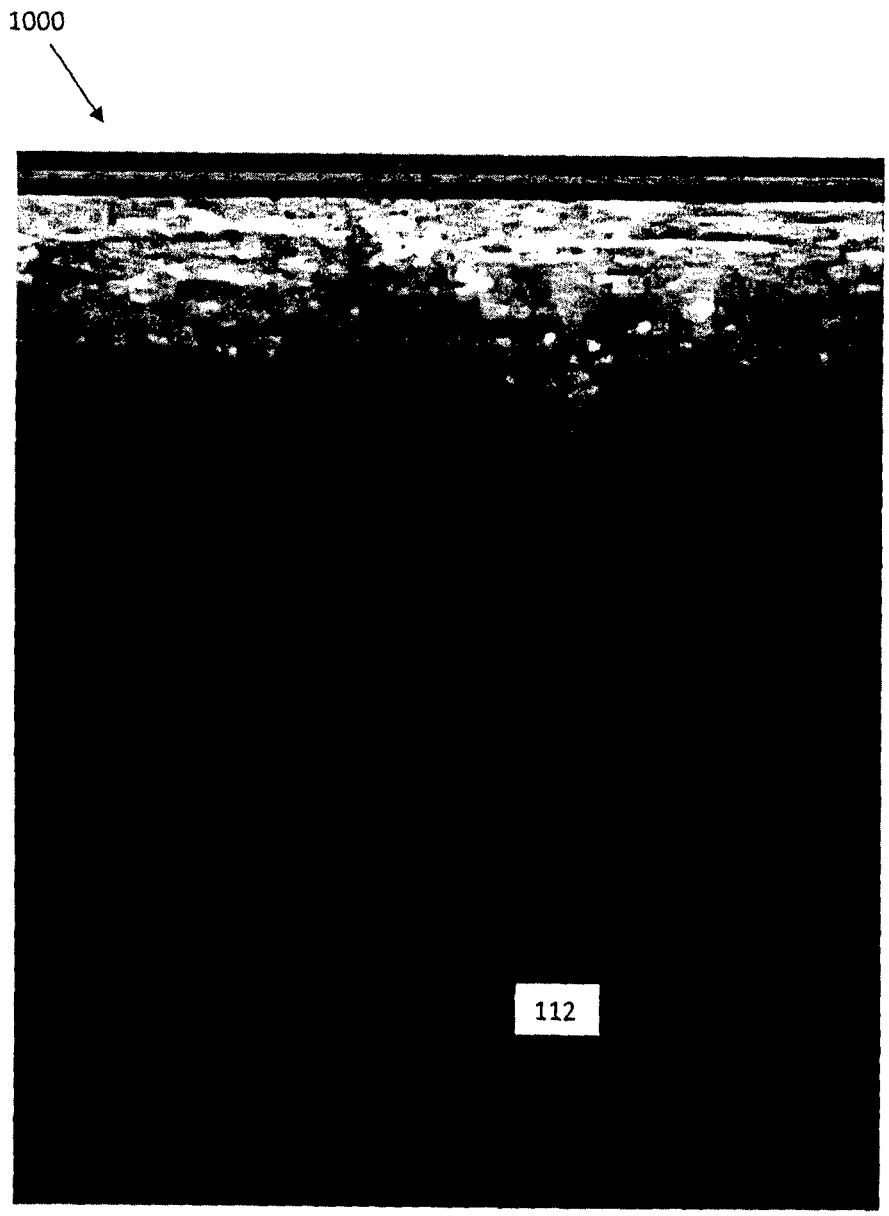

FIG. 10 demonstrates the ability of the needle probe 102 to inject a gas into biological tissue 112 during OCT imaging. In this case, air was injected into the biological tissue 112 through the needle probe 102. Note the marked change in image 1000 quality as the gas has replaced the liquid in the tissue 112 compared to FIG. 9.

Figure 11:
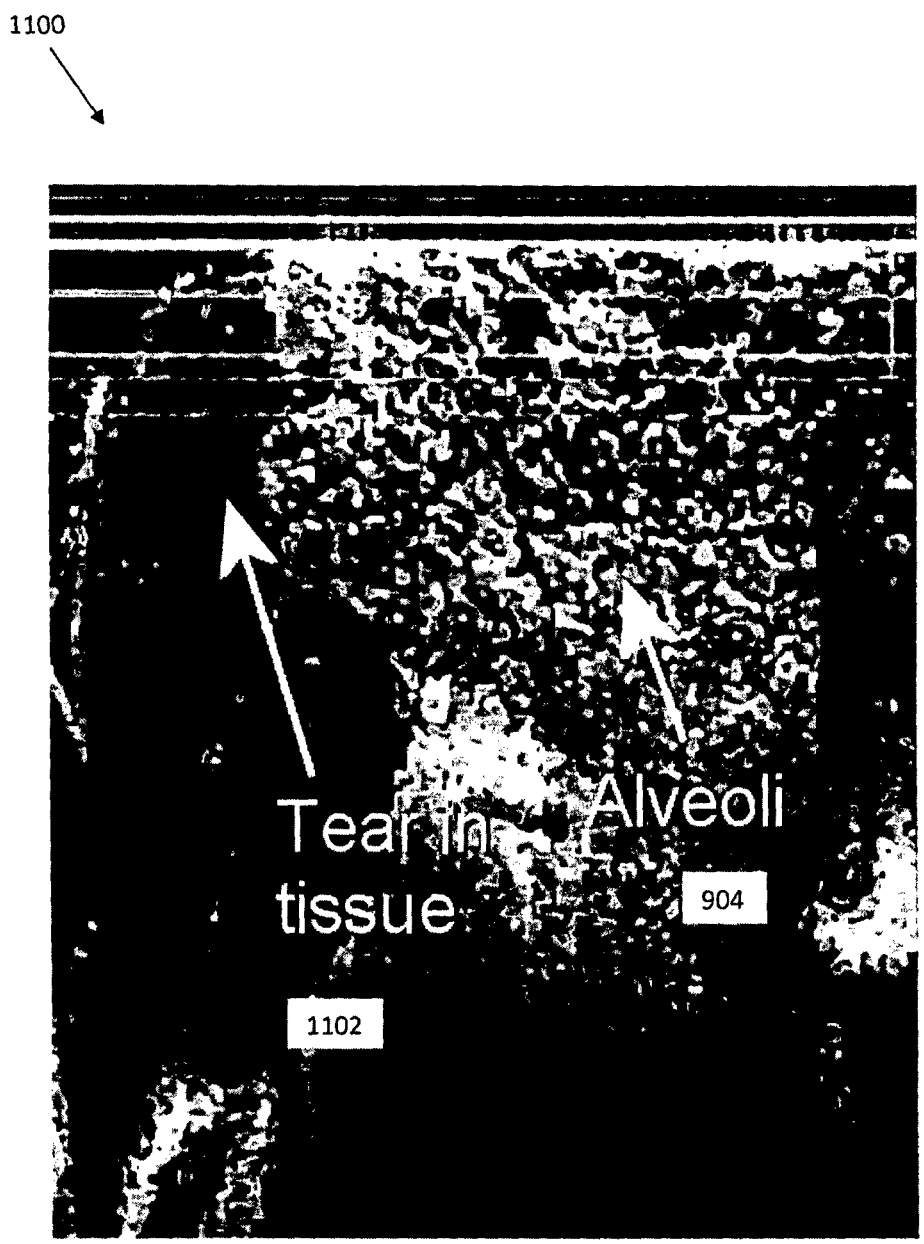

FIG. 11 demonstrates the ability of the needle probe 102 to inject fluids other than saline. In this case, glycerol has been injected through the needle probe 102 during OCT imaging. Note that glycerol has a different refractive index to saline and greatly improves the image penetration depth of the OCT image. Glycerol is also noted to be an optical clearing agent (see Genina, E. A., A. N. Bashkatov, and V. V. Tuchin, Tissue optical immersion clearing. *Expert Review of Medical Devices,* 2010. 7(6): pp. 825-842). A large collection of alveoli 904 are visible in this scan, appearing as a honeycomb structure in the middle region of the image 1100.

Also note that the glycerol, because of its high viscosity, was used to render tear 1102 in the tissue 112, demonstrating that the fluid injected by the needle probe 102 can be used to effect a structural change to the tissue 112. This can yield information about the mechanical properties (resistance to tearing) of a region of interest of biological tissue sample analysed by the probe 102.

Example 2: Determination of Mechanical Properties

In this example the needle probe 102 was again inserted into a porcine lung tissue sample 112, but held stationary during imaging. Saline fluid was pumped in a pulsatile manner, exerting stress on tissue 112 adjacent to the imaging needle probe 102. A sequence of 1D depth scans (A-scans) were acquired at the same location in tissue 112. These scans were sequentially aggregated to construct an image 1200 shown in FIG. 12. The image 1200 depicts movement of the tissue 112 in the direction of the light beam transmitted from the needle probe 102 during pumping of the fluid into the region of interest of the tissue 112. This is referred to as an M-mode (Motion-mode) image in the scientific literature for OCT.

Figure 12:
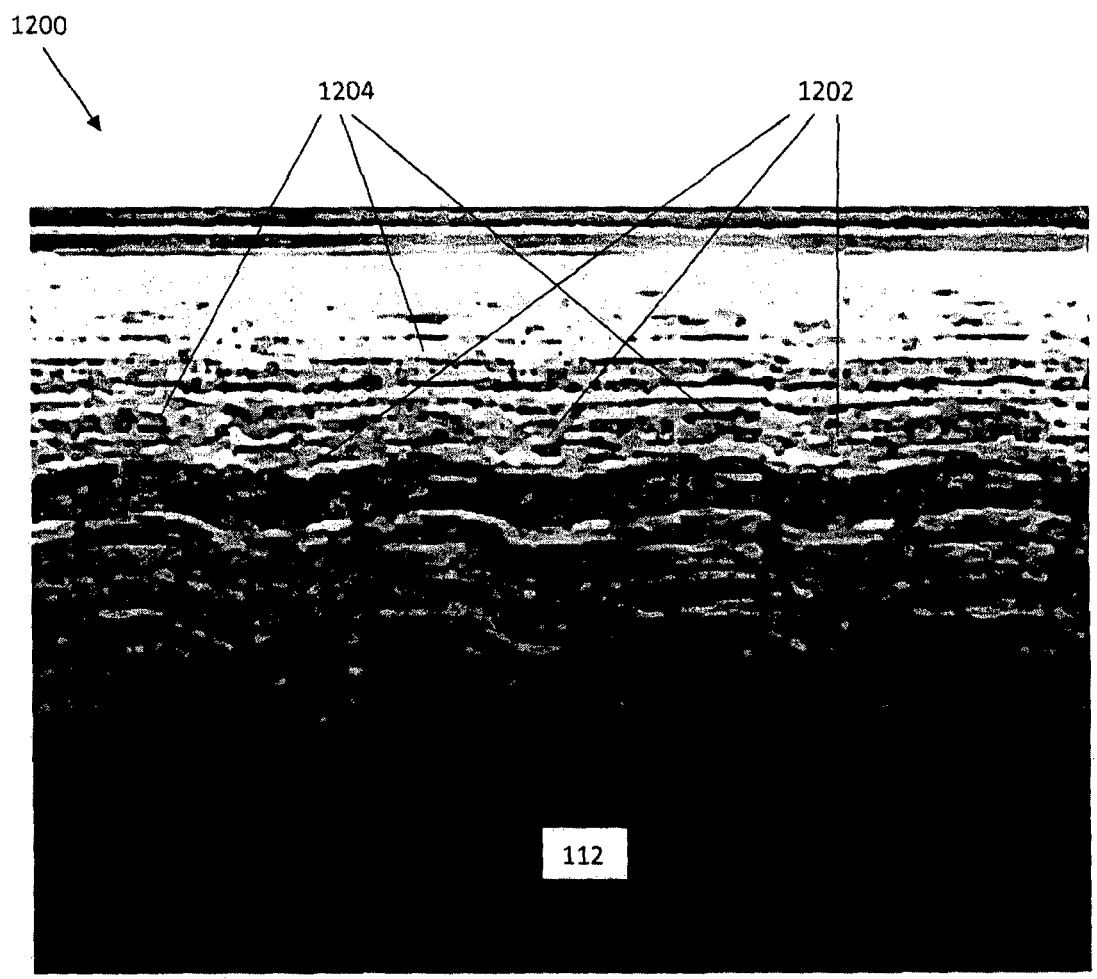

A vertical column of the image 1200 of FIG. 12 constitutes a single 1-D depth scan (A-scan) acquired by the OCT needle probe 102 at a point in time. The A-scans are sequentially stacked horizontally to build the image 1200 of the region of interest of the tissue 112 over time. The periodic pattern apparent in the image 1200 by "peaks" 1202 and "troughs" 1204 is due to the motion of the tissue 112 undergoing stress from the pulsatile pumping of saline fluid. The degree of movement between the "peaks" 1202 and "troughs" 1204 is indicative of the mechanical properties of the tissue 112. For example, stiffer tissue allows less movement while more elastic tissue would allow greater movement.

The reference to prior art that is made herein does not constitute an admission that that prior art is part of the common general knowledge of a person skilled in the art in Australia or anywhere else in the world.

Although the invention has been described with reference to particular examples, it will be appreciated by those skilled in the art that the invention may be embodied in many other forms.

Throughout the present specification, the use of the singular includes the plural unless specifically stated otherwise.

The invention claimed is:

1. A method for characterising a physical property of a region of interest within or between biological tissue using an optical imaging technique, the method comprising:
   inserting at least a portion of an elongated probe body of a probe into the region of interest, the probe body being formed from a rigid material and having a fluid opening that is fixed relative to the elongated probe body on a side of the elongated probe body, the probe having a conduit at least partially positioned within the elongated probe body and an optical waveguide being at least partially positioned within the conduit;
   directing a fluid through the conduit to the fluid opening and expelling the fluid through the fluid opening towards the region of interest in a direction traversal to the elongated probe body ;
   directing transmission of electromagnetic radiation from the probe towards the region of interest in a same direction transversal to the elongated probe body as the direction in which fluid is expelled through the fluid opening using a reflector, wherein the reflector is at least partially positioned within the elongated probe body and is configured to receive electromagnetic radiation from the optical waveguide along the length of the elongated probe body and to redirect the electromagnetic radiation in the direction transversal to the elongated probe body from a position that is fixed relative to the elongated probe body;
   receiving electromagnetic radiation from the region of interest by the probe; and
   analysing the received electromagnetic radiation received by the probe from the region of interest to differentiate between tissue types based on the analysis of the electromagnetic radiation received by the probe.

2. The method of claim 1 wherein directing the fluid comprises directing the fluid substantially exclusively into the proximity of the region of interest.

3. The method of claim 1 wherein the probe is a needle probe.

4. The method of claim 1 wherein the method comprises moving the elongated probe body in a direction along an axis of the elongated probe body during directing transmission of the electromagnetic radiation and wherein the method comprises rotating the elongated probe body in a direction around an axis of the elongated probe body during directing transmission of the electromagnetic radiation.

5. The method of claim 1 wherein the method comprises characterising the property of the region of interest as a function of three spatial dimensions.

6. The method of claim 1 wherein directing the electromagnetic radiation is conducted multiple times where those times may be before and/or after an onset of directing the fluid to the region of interest.

7. The method of claim 1 wherein directing the transmission of the electromagnetic radiation includes directing and receiving the electromagnetic radiation through at least one selected from a group consisting of a portion that is substantially transmissive for the electromagnetic radiation and a further opening of the elongated probe body.

8. The method of claim 1 wherein the optical imaging technique includes at least one of selected from a group consisting of optical coherence tomography (OCT) imaging, confocal imaging, and fluorescence microscopy.

9. The method of claim 1 comprising using the characterised physical property to characterise a mechanical property of the biological tissue within the region of interest.

10. The method of claim 1 wherein the fluid includes at least one selected from a group consisting of an optical clearing agent, an optical contrast agent, a dye, a fluorescent label, and bioluminescent label.

11. The method of claim 1 wherein the fluid comprises a therapeutic agent and wherein directing the fluid to the region of interest comprises directing the therapeutic agent to the identified specific region of interest.

12. The method of claim 1 wherein the fluid comprises a therapeutic agent and directing the electromagnetic radiation comprises monitoring an effect of the therapeutic agent on the identified specific region of interest.

13. A method for characterising a physical property of a region of interest within or between biological tissue using an optical imaging technique, the method comprising:
   inserting at least a portion of an elongated probe body of a probe into the region of interest, the elongated probe body being formed from a rigid material and having a fluid opening that is fixed relative to the elongated probe body on a side of the elongated probe body, the probe having a conduit at least partially positioned within the elongated probe body and an optical waveguide at least partially positioned within the conduit;
   directing a fluid through the conduit to the fluid opening and expelling the fluid through the fluid opening towards the region of interest in a direction transversal to the elongated probe body;
   directing transmission of electromagnetic radiation from the probe towards the region of interest in a same direction transversal to the elongated probe body as the direction in which fluid is expelled through the fluid opening using a reflector, wherein the reflector is at least partially positioned within the elongated probe body and is configured to receive electromagnetic radiation from the optical waveguide along the length of the elongated probe body and to redirect the electromagnetic radiation in the direction transversal to the elongated probe body from a position that is fixed relatve to the elongated probe body;
   receiving first and second types of electromagnetic radiation from the region of interest using the probe; and
   analysing the received first and second types of electromagnetic radiation to differentiate between tissue types based on the analysis of the electromagnetic radiation received by the probe.

14. The method of claim 13 wherein the first type of the received electromagnetic radiation is radiation that has been directed to the region of interest by the probe and is reflected by the region of interest and wherein the second type of electromagnetic radiation is fluorescent radiation that is generated by the region of interest or by fluorescence markers that are present in the region of interest.

15. A system for characterising a physical property of a biological tissue using an optical imaging technique, the system comprising:
   a probe including:
      an elongated probe body for at least partial insertion into a region of interest within or between the biological tissue, the elongated probe body being formed from a rigid material and having a fluid opening that is fixed relative to the elongated probe body on a side of the elongated probe body and that is in use positioned within or between the biological tissue,
      a conduit at least partially positioned within the elongated probe body, wherein the conduit is configured to convey a fluid along a length of the elongated probe body from a fluid reservoir to the fluid opening of the elongated probe body and to expel the fluid through the fluid opening towards the region of interest in a direction that is transversal to the elongated probe body,
      an optical waveguide at least partialy positioned within the conduit, and
      a reflector configured to receive electromagnetic radiation from the optical waveguide along the length of the elongated probe body and to direct transmission of the electromagnetic radiation from a position that is fixed relative to the probe body towards the region of interest in a same direction transversal to the elongated probe body as the direction in which fluid is expelled through the fluid opening, wherein the probe is further configured to receive electromagnetic radiation from the region of interest;
   the fluid reservoir coupled to the conduit; and
   an analyser configured to analyze electromagnetic radiation received by the probe from the region of interest and to differentiate between tissue types based on the analysis of the electromagnetic radiation received by the probe.

16. The system of claim 15 wherein the probe is arranged such that the transmission of the electromagnetic radiation between the probe and the region of interest is conducted through the at least one fluid opening.

17. The system of claim 15 wherein the elongated probe body comprises at least one of: a portion that is substantially transmissive for the electromagnetic radiation or a further opening through which the electromagnetic radiation is in use directed; and
   wherein a location from which in use the electromagnetic radiation is directed is fixed relative to the probe body and is in the proximity of the at least one fluid opening.

18. The system of claim 15 wherein the system is arranged for optical coherence tomography (OCT) imaging or fluorescence imaging.

* * * * *